(12) United States Patent
Ben-David et al.

(10) Patent No.: US 8,615,294 B2
(45) Date of Patent: Dec. 24, 2013

(54) ELECTRODE DEVICES FOR NERVE STIMULATION AND CARDIAC SENSING

(75) Inventors: Tamir Ben-David, Tel Aviv (IL); Shai Ayal, Jerusalem (IL); Ehud Cohen, Ganei Tikva (IL); Yossi Gross, Moshav Mazor (IL); Nir Schain, Tel Aviv (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1379 days.

(21) Appl. No.: 12/228,630

(22) Filed: Aug. 13, 2008

(65) Prior Publication Data

US 2010/0042186 A1 Feb. 18, 2010

(51) Int. Cl.
*A61N 1/00* (2006.01)

(52) U.S. Cl.
USPC .............................................. 607/2

(58) Field of Classification Search
USPC ............................................ 607/2, 3, 17, 18
See application file for complete search history.

(56) References Cited

U.S. PATENT DOCUMENTS

| | | |
|---|---|---|
| 4,010,755 A | 3/1977 | Preston |
| 4,026,300 A | 5/1977 | DeLuca et al. |
| 4,161,952 A | 7/1979 | Kinney et al. |
| 4,573,481 A | 3/1986 | Bullara |
| 4,602,624 A | 7/1986 | Naples et al. |
| 4,628,942 A | 12/1986 | Sweeney et al. |
| 5,095,905 A | 3/1992 | Klepinski |
| 5,143,067 A | 9/1992 | Rise et al. |
| 5,170,802 A | 12/1992 | Mehra |
| 5,199,430 A | 4/1993 | Fang et al. |
| 5,203,326 A | 4/1993 | Collins |
| 5,224,491 A | 7/1993 | Mehra |
| 5,243,980 A | 9/1993 | Mehra |
| 5,282,468 A | 2/1994 | Klepinski |
| 5,334,221 A | 8/1994 | Bardy |
| 5,344,438 A | 9/1994 | Testerman et al. |
| 5,356,425 A | 10/1994 | Bardy et al. |
| 5,411,531 A | 5/1995 | Hill et al. |
| 5,423,872 A | 6/1995 | Cigaina |
| 5,487,756 A | 1/1996 | Kallesoe et al. |
| 5,507,784 A | 4/1996 | Hill et al. |

(Continued)

FOREIGN PATENT DOCUMENTS

DE 19847446 4/2000
EP 0688577 12/1995

(Continued)

OTHER PUBLICATIONS

Office Action, issued Oct. 24, 2008 during the prosecution of Applicants' U.S. Appl. No. 11/022,011.

(Continued)

*Primary Examiner* — George Manuel
*Assistant Examiner* — Minh Duc Pham
(74) *Attorney, Agent, or Firm* — Sughrue Mion, PLLC (57) ABSTRACT

Apparatus is provided for application to a nerve of a subject, the apparatus comprising an electrode device, which comprises a housing, which is configured to be placed at least partially around the nerve, so as to define an outer surface of the electrode device and an inner surface that faces the nerve. The electrode device further comprises one or more first electrode contact surfaces, fixed to the inner surface of the housing, and one or more second electrode contact surfaces, fixed to the outer surface of the housing. Other embodiments are also described.

21 Claims, 7 Drawing Sheets

(56) References Cited

U.S. PATENT DOCUMENTS

| | | |
|---|---|---|
| 5,634,462 A | 6/1997 | Tyler et al. |
| 5,690,681 A | 11/1997 | Geddes et al. |
| 5,700,282 A | 12/1997 | Zabara |
| 5,800,470 A | 9/1998 | Stein et al. |
| 5,824,027 A | 10/1998 | Hoffer et al. |
| 5,833,664 A | 11/1998 | Seare, Jr. |
| 5,893,881 A | 4/1999 | Elsberry et al. |
| 5,916,239 A | 6/1999 | Geddes et al. |
| 5,938,596 A | 8/1999 | Woloszko et al. |
| 6,006,134 A | 12/1999 | Hill et al. |
| 6,073,048 A | 6/2000 | Kieval et al. |
| H1905 H | 10/2000 | Hill |
| 6,161,029 A | 12/2000 | Spreigl et al. |
| 6,178,349 B1 | 1/2001 | Kieval |
| 6,230,061 B1 | 5/2001 | Hartung |
| 6,292,695 B1 | 9/2001 | Webster, Jr. et al. |
| 6,292,703 B1 | 9/2001 | Meier et al. |
| 6,298,268 B1 | 10/2001 | Ben-Haim et al. |
| 6,308,105 B1 | 10/2001 | Duysens et al. |
| 6,317,631 B1 | 11/2001 | Ben-Haim et al. |
| 6,363,279 B1 | 3/2002 | Ben-Haim et al. |
| 6,445,953 B1 | 9/2002 | Bulkes et al. |
| 6,456,866 B1 | 9/2002 | Tyler et al. |
| 6,463,324 B1 | 10/2002 | Ben-Haim et al. |
| 6,542,774 B2 | 4/2003 | Hill et al. |
| 6,564,096 B2 | 5/2003 | Mest |
| 6,600,956 B2 | 7/2003 | Maschino et al. |
| 6,611,713 B2 | 8/2003 | Schauerte |
| 6,628,987 B1 | 9/2003 | Hill et al. |
| 6,684,105 B2 | 1/2004 | Cohen et al. |
| 6,712,772 B2 | 3/2004 | Cohen et al. |
| RE38,705 E | 2/2005 | Hill et al. |
| 6,850,801 B2 | 2/2005 | Kieval et al. |
| 6,865,416 B2 | 3/2005 | Dev et al. |
| 6,866,657 B2 | 3/2005 | Shchervinsky |
| 6,907,295 B2 | 6/2005 | Gross et al. |
| 6,934,583 B2 | 8/2005 | Weinberg et al. |
| 6,937,897 B2 | 8/2005 | Min et al. |
| 6,985,774 B2 | 1/2006 | Kieval et al. |
| 7,020,530 B1 | 3/2006 | Ideker et al. |
| 7,027,876 B2 | 4/2006 | Casavant et al. |
| 7,087,053 B2 | 8/2006 | Vanney |
| 7,113,816 B2 | 9/2006 | Matsukawa et al. |
| 7,123,961 B1 | 10/2006 | Kroll et al. |
| 7,139,607 B1 | 11/2006 | Shelchuk |
| 7,167,748 B2 | 1/2007 | Ben-Haim et al. |
| 7,212,870 B1 | 5/2007 | Helland |
| 7,218,971 B2 | 5/2007 | Heil et al. |
| 7,225,016 B1 | 5/2007 | Koh |
| 7,236,821 B2 | 6/2007 | Cates et al. |
| 7,245,967 B1 | 7/2007 | Shelchuk |
| 7,248,930 B1 | 7/2007 | Woloszko et al. |
| 7,269,457 B2 | 9/2007 | Shafer et al. |
| 7,321,793 B2 | 1/2008 | Ben Ezra et al. |
| 7,421,297 B2 * | 9/2008 | Giftakis et al. ............... 607/45 |
| 7,584,004 B2 | 9/2009 | Caparso et al. |
| 7,623,926 B2 | 11/2009 | Rossing et al. |
| 7,809,442 B2 | 10/2010 | Bolea et al. |
| 7,840,266 B2 | 11/2010 | Libbus et al. |
| 7,996,092 B2 | 8/2011 | Mrva et al. |
| 8,155,757 B1 | 4/2012 | Neisz et al. |
| 8,214,056 B2 | 7/2012 | Hoffer et al. |
| 2002/0099419 A1 | 7/2002 | Cohen et al. |
| 2002/0161415 A1 | 10/2002 | Cohen et al. |
| 2003/0045909 A1 | 3/2003 | Gross et al. |
| 2003/0045914 A1 | 3/2003 | Gross et al. |
| 2003/0100933 A1 | 5/2003 | Ayal et al. |
| 2004/0006311 A1 | 1/2004 | Shchervinsky |
| 2004/0006331 A1 | 1/2004 | Shchervinsky |
| 2004/0193231 A1 | 9/2004 | David et al. |
| 2004/0199210 A1 | 10/2004 | Shelchuk |
| 2005/0010265 A1 | 1/2005 | Baru Fassio et al. |
| 2005/0065553 A1 | 3/2005 | Ben-Ezra et al. |
| 2005/0131467 A1 | 6/2005 | Boveja |
| 2005/0149154 A1 | 7/2005 | Cohen et al. |
| 2005/0187584 A1 | 8/2005 | Denker et al. |
| 2005/0197675 A1 | 9/2005 | David et al. |
| 2005/0261672 A1 | 11/2005 | Deem et al. |
| 2005/0267542 A1 | 12/2005 | David et al. |
| 2005/0273138 A1 | 12/2005 | To et al. |
| 2006/0052831 A1 | 3/2006 | Fukui |
| 2006/0074449 A1 | 4/2006 | Denker et al. |
| 2006/0100668 A1 | 5/2006 | Ben-David et al. |
| 2006/0106441 A1 | 5/2006 | Ayal et al. |
| 2006/0136024 A1 | 6/2006 | Cohen et al. |
| 2006/0167501 A1 | 7/2006 | Ben-David et al. |
| 2006/0195170 A1 | 8/2006 | Cohen et al. |
| 2006/0206153 A1 | 9/2006 | Libbus et al. |
| 2006/0206154 A1 | 9/2006 | Moffitt et al. |
| 2006/0206155 A1 | 9/2006 | Ben-David et al. |
| 2006/0206159 A1 | 9/2006 | Moffitt et al. |
| 2006/0217772 A1 | 9/2006 | Libbus et al. |
| 2006/0229677 A1 | 10/2006 | Moffitt et al. |
| 2006/0241697 A1 * | 10/2006 | Libbus et al. ............... 607/2 |
| 2006/0241725 A1 | 10/2006 | Libbus et al. |
| 2006/0241733 A1 | 10/2006 | Zhang et al. |
| 2006/0247607 A1 | 11/2006 | Cornelius et al. |
| 2006/0265027 A1 | 11/2006 | Vaingast et al. |
| 2006/0271108 A1 | 11/2006 | Libbus et al. |
| 2006/0271115 A1 | 11/2006 | Ben-Ezra et al. |
| 2006/0271137 A1 | 11/2006 | Stanton-Hicks |
| 2006/0282145 A1 | 12/2006 | Caparso et al. |
| 2007/0027487 A1 | 2/2007 | Mika |
| 2007/0150034 A1 | 6/2007 | Rooney et al. |
| 2007/0162079 A1 | 7/2007 | Shemer et al. |
| 2007/0179543 A1 | 8/2007 | Ben-David et al. |
| 2007/0179558 A1 * | 8/2007 | Gliner et al. ............... 607/45 |
| 2007/0203527 A1 | 8/2007 | Ben-David et al. |
| 2007/0239243 A1 * | 10/2007 | Moffitt et al. ............... 607/118 |
| 2007/0255320 A1 | 11/2007 | Inman et al. |
| 2008/0004673 A1 | 1/2008 | Rossing et al. |
| 2008/0021504 A1 * | 1/2008 | McCabe et al. ............... 607/9 |
| 2008/0065158 A1 | 3/2008 | Ben-Ezra et al. |
| 2008/0065184 A1 | 3/2008 | Hoffer et al. |
| 2008/0086180 A1 | 4/2008 | Ben-Ezra et al. |
| 2008/0086185 A1 * | 4/2008 | Amurthur et al. ............... 607/60 |
| 2008/0109045 A1 * | 5/2008 | Gross et al. ............... 607/39 |
| 2008/0132983 A1 | 6/2008 | Cohen et al. |
| 2008/0172116 A1 | 7/2008 | Mrva et al. |
| 2009/0005845 A1 | 1/2009 | David et al. |
| 2009/0259315 A1 | 10/2009 | Banik |
| 2009/0275996 A1 | 11/2009 | Burnes et al. |
| 2010/0047376 A1 | 2/2010 | Imbeau et al. |
| 2010/0241195 A1 | 9/2010 | Meadows et al. |
| 2010/0241207 A1 | 9/2010 | Bluger |
| 2010/0312320 A1 | 12/2010 | Faltys et al. |
| 2011/0160827 A1 | 6/2011 | Bonde et al. |
| 2011/0196445 A1 | 8/2011 | Bolea et al. |
| 2011/0202106 A1 | 8/2011 | Bolea et al. |
| 2012/0095540 A1 | 4/2012 | Wahlstrand et al. |
| 2012/0130463 A1 | 5/2012 | Ben-David |
| 2012/0197371 A1 | 8/2012 | Neisz et al. |

FOREIGN PATENT DOCUMENTS

| | | |
|---|---|---|
| EP | 0865800 | 9/1998 |
| EP | 1785160 | 5/2007 |
| WO | WO 0110357 | 2/2001 |
| WO | WO 0222206 | 3/2002 |
| WO | WO 02087683 | 11/2002 |
| WO | WO 03018113 | 3/2003 |
| WO | WO 03094693 | 11/2003 |
| WO | WO 03099373 | 12/2003 |
| WO | WO 03099377 | 12/2003 |
| WO | WO 200428624 | 4/2004 |
| WO | WO 200447914 | 6/2004 |
| WO | WO 2004052444 | 6/2004 |
| WO | WO 2004103455 | 12/2004 |
| WO | WO 2004110549 | 12/2004 |
| WO | WO 2004110550 | 12/2004 |
| WO | WO 2006126201 | 11/2006 |

(56) References Cited

FOREIGN PATENT DOCUMENTS

WO  WO 2007053065  5/2007
WO  WO 200807630  1/2008

OTHER PUBLICATIONS

Office Action, issued Dec. 8, 2009 during the prosecution of Applicants' U.S. Appl. No. 11/347,120.
European Search Report, issued Aug. 27, 2009 during the prosecution of Applicants' European Patent Application No. EP 09 25 1749.
Supplementary European Search Report, issued Nov. 4, 2009 during the prosecution of Applicants' European Patent Application No. EP 03 72 3040.
Akselrod, S. et al., (1981) "Power spectrum analysis of heart rate fluctuation: a quantitative probe of beat-to-beat cardiovascular control," *Science*, 213: 220-222.
Baratta, R. et al., (1989) "Orderly stimulation of skeletal muscle motor units with tripolar nerve cuff electrode," *IEEE Transactions on Biomedical Engineering*, 36(1): 836-843.
Billette, J. et al., (1975) "Roles of the AV junction in determining the ventricular response to atrial fibrillation," *Can. J. Physiol. Pharmacal.*, 53(4): 575-585.
Bluemel, K.M. et al., (1990) "Parasympathetic Postganglionic Pathways to the Sinoatrial Node," *The American Journal of Physiology*, 259(5 Pt 2): H1504-10.
Borovikova, L.V. et al., (2000) "Vagus nerve stimulation attenuates the systemic inflammatory response to endotoxin," *Nature*, 405(6785): 458-462.
Chen, et al., (1998) "Intracardiac Stimulation of Human Parasympathetic Nerve Fibers Induces Negative Dromotropic Effects: implication with the lesions of radiofrequency catheter ablation," *Journal of Cardiovascular Electrophysiology*, 9(3): 245-252.
Cooper, et al., (1980) "Neural effects on Sinus Rate and Atrial Ventricular Conduction Produced by Electrical Stimulation from a Transvenous Electrode Catheter in the Canine Right Pulmonary Artery," *Circ Res* vol. 46(1): 48-57.
De Ferrari, G.M., (1991) "Vagal reflexes and survival during acute myocardial ischemia in conscious dogs with healed myocardial infarction," *Am. J. Physiol.*, 261(1 Pt 2): H63-H69.
Deurloo, K.E. et al., (1998) "Transverse tripolar stimulation of peripheral nerve: a modeling study of spatial selectivity," *Med. Bio. Eng. Comput.*, 36: 66-74.
Fitzpatrick, D.M. et al., (1991) "A nerve cuff design for the selective activation and blocking of myelinated nerve fibers," *Ann. Intl. Conf. of the IEEE Eng. in Med. and Bio.*, 13(2): 906-907.
Garrigue, S. et al., (1998) "Post-ganglionic vagal stimulation of the atrioventricular node reduces ventricular rate during atrial fibrillation," *Pacing and Clinical Electrophysiology*, 21(4), Part II, 878.
Goldberger, J.J. et al., (1999) "New technique for vagal nerve stimulation," *J Neurosci Methods*, 91(1-2): 109-114.
Goodall, E.V. et al., (1996) "Position-selective activation of peripheral nerve fibers with a cuff electrode," *IEEE Transactions on Biomedical Engineering*, 43(8): 851-856.
Grill, W.M. et al., (1997) "Inversion of the current-distance relationship by transient depolarization," *IEEE Transactions on Biomedical Engineering*, 44(1): 1-9.
Hayashi, H. et al., (1998) "Different effects of class Ic and III antiarrhythmic drugs on vagotonic atrial fibrillation in the canine heart," *Journal of Cardiovascular Pharmacology*, 31: 101-107.
Higgins, C.B., (1973) "Parasympathetic control of the heart," *Pharmacol. Rev.*, 25: 119-155.
Jideus, L., (2001) "Atrial Fibrillation After Coronary Artery Bypass Surgery. A Study of Causes and Risk Factors," *Comprehensive Summaries of Uppsala Dissertations from the Faculty of Medicine*, 1093: 1-56.
Jones, J.F.X. et al., (1995) "Heart rate responses to selective stimulation of cardiac vagal C fibres in anaesthetized cats, rats and rabbits," *J. Physiol.*, 489(Pt. 1): 203-211.

Kamath, M. et al., (1992) "Effect of vagal nerve electrostimulation on the power spectrum of heart rate variability in man," PACE vol. 15, *Clinical Electrophysiology*, 15: 235-243.
Kwan, H. et al., (2001) "Cardiovascular adverse drug reactions during initiation of antiarrhythmic therapy for atrial fibrillation," *Canadian Journal of Hospital Pharmacists*, 54(1): 10-14.
Lazzara, R. et al., (1973) "Selective in situ Parasympathetic control of the canine sinoatrial and atrioventricular nodes," *Circulation Research*, 32: 393: 401.
Lemery, R. et al., (2006) "Feasability study of endocardial mapping of ganglionated plexuses during catheter ablation of atrial fibrillation." *Heart Rhythm*, 3: 387-396.
Li, D. et al., (1999) "Promotion of Atrial Fibrillation by Heart Failure in Dogs. Atrial Remodeling of a Different Sort," *Circulation*, 100(1): 87-95.
Manfredi, M., (1970) "Differential Block of Conduction of Larger Fibers in Peripheral Nerve by Direct Current," *Archives italiennes de biologie*, 108(1): 52-71.
Martin, P.J. et al., (1983) "Phasic effects of repetitive vagal stimulation on atrial contraction." *Circulation Research*: vol. 52(6): 657-663.
Morady, F. et al., (1990) "Effects of resting vagal tone on accessory atrioventricular connections," *Circulation*: 81(1): 86-90.
Mushahwar, V.K. et al., (2000) "Muscle recruitment through electrical stimulation of the lumbo-sacral spinal cord," *IEEE Transactions on Biomedical Engineering*, 8(1): 22-29.
Naples, G.G. et al., (1988) "A spiral nerve cuff electrode for peripheral nerve stimulation," *IEEE Transactions on Biomedical Engineering*, 35(11): 905-916.
Quan, K.J. et al., (2001) "Endocardial stimulation of efferent parasympathetic nerves to the atrioventricular node in humans: optimal stimulation sites and the effects of digoxin," *Journal of Interventional Cardiac Electrophysiology*, 5: 145-152.
Randall, W.C., ed., (1977) *Neural Regulation of the Heart*, Oxford University Press, 100-106.
Rijkhoff, N.J. et al., (1994) "Acute animal studies on the use of anodal block to reduce urethral resistance in sacral root stimulation," *IEEE Transactions on Rehabilitation Engineering*, 2(2): 92-99.
Rijkhoff, N.J. et al., (1998) "Orderly recruitment of motoneurons in an acute rabbit model," *Proc. of the Annual Conf. of the IEEE Engineering in Medicine and Biology Society*, 20(5): 2564-2565.
Schauerte, P. et al., (2001) "Catheter stimulation of cardiac parasympathetic nerves in humans: A novel approach to the cardiac autonomic nervous system," *Circulation*, 104: 2430-2435.
Schauerte, P. et al., (1973) "Transvenous parasympathetic cardiac nerve stimulation for treatment of tachycardiac atrial fibrillation," *Tachycarde Rhythmusstorungen*, 89: 766-773.
Schauerte, P. et al., (1999) "Ventricular rate control during atrial fibrillation by cardiac parasympathetic nerve stimulation: A transvenous approach," *Journal of the American College of Cardiology*, 34(7): 2043-2050.
Stramba-Badiale, M. et al., (1991) "Sympathetic-parasympathetic interaction and accentuated antagonism in conscious dogs," *American Journal of Physiology*, 260: H335-H340.
Sweeney, J.D. et al., (1990) "An asymmetric two electrode cuff for generation of unidirectionally propagated action potentials," *IEEE Transactions on Biomedical Engineering*, BME-33(6): 541-549.
Sweeney, J.D. et al., (1986) "A nerve cuff technique for selective excitation of peripheral nerve trunk regions," *IEEE Transactions on Biomedical Engineering*, 37(7): 706-715.
Takei, M. et al., (2001) "Vagal stimulation prior to atrial rapid pacing protects the atrium from electrical remodeling in anesthetized dogs," *Jpn. Circ. J.*, 65(12): 1077-1081.
Tarver, W.B. et al., (1992) "Clinical experience with a helical bipolar stimulating lead," *Pace*: vol. 15, October, Part II: 1545-1556.
Tsuboi, M. et al., (2000) "Inotropic, chronotropic, and dromotropic effects mediated via parasympathetic ganglia in the dog heart," *Am. J. Physiol. Heart Circ. Physiol.*, 279: H1201-H1207.
Ungar, I.J. et al., (1986) "Generation of unidirectionally propagating action potentials using a monopolar electrode cuff," *Annals of Biomedical Engineering*, 14: 437-450.

(56) References Cited

OTHER PUBLICATIONS

Van Den Honert, C. et al., (1981) "A technique for collision block of peripheral nerve: Frequency dependence," *MP-12, IEEE Transactions on Biomedical Engineering*: 28: 379-382.

Van Den Honert, C. et al., (1979) "Generation of unidirectionally propagated action potentials in a peripheral nerve by brief stimuli," *Science*: 206: 1311-1312.

Vanoli, E. et al., (1991) "Vagal stimulation and prevention of sudden death in conscious dogs with a healed myocardial infarction," *Circ. Res.*, 68(5): 1471-1481.

Veraart, C. et al., (1993) "Selective control of muscle activation with a multipolar nerve cuff electrode," *IEEE Transactions on Biomedical Engineering*, 40(7): 640-653.

Vincenzi, F.F. et al., (1963) "Release of Autonomic Mediators in Cardiac Tissue by Direct Subthreshold Electrical Stimulation," *J Pharmacol Exp Ther.*, Aug. 141: 185-194.

Wallick, D.W. et al., (2001) "Selective AV nodal vagal stimulation improves hemodynamics during actute atrial fibrillation in dogs," *Am. J. Physiol. Heart Circ. Physiol.*, 281: H1490-H1497.

Wang, H. et al., (2003) "Nicotinic acetylcholine receptor alpha-7 subunit is an essential regulator of inflammation," *Nature*, 421: 384-388.

Waninger, M.S. et al., (2000) "Electrophysiological control of ventricular rate during atrial fibrillation," *Pacing and Clinical Physiology*, 23(8): 1239-44.

Wijffels, M.C. et al., (1995) "Atrial fibrillation begets atrial fibrillation," *Circulation*, 92: 1954-1968.

Zhang, Y. et al., (2005) "Chronic atrioventricular nodal vagal stimulation: first evidence for long-term ventricular rate control in canine atrial fibrillation model," *Circulation*, 112: 2904-2911.

Zhang, Y. et al., (2002) "Optimal ventricular rate slowing during atrial fibrillation by feedback AV nodal-selective vagal stimulation," *Am. J. Physiol. Heart Circ. Physiol.*, 282: H1102-H1110.

A Supplementary European Search Report dated Aug. 16, 2010, which issued during the prosecution of Applicant's European Patent Application No. 03725560.

An Examination Report dated Feb. 7, 2011, which issued during the prosecution of Applicant's European Patent Application No. 03725560.

Final Office Action issued in Applicant's U.S. Appl. No. 12/012,366 on Dec. 2, 2011.

An Office Action dated Nov. 21, 2012, which issued during the prosecution of U.S. Appl. No. 12/952,058.

An Office Action dated Jan. 22, 2013, which issued during the prosecution of U.S. Appl. No. 13/022,279.

\* cited by examiner

ELECTRODE DEVICES FOR NERVE STIMULATION AND CARDIAC SENSING

FIELD OF THE INVENTION

The present invention relates generally to medical electrical stimulation and sensing devices, and specifically to methods and devices for stimulation of nerves and/or sensing of electrical cardiac signals.

BACKGROUND OF THE INVENTION

A number of patents and articles describe methods and devices for stimulating nerves to achieve a desired effect. Often these techniques include a design for an electrode or electrode cuff.

The control unit of an implantable electronic device such as a pacemaker or a defibrillator typically has two portions: a metal can, which includes the circuitry of the device, and a non-metallic header, which provides connection points for leads.

U.S. Pat. No. 6,907,295 to Gross et al., which is assigned to the assignee of the present application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

US Patent Application Publication 2006/0106441 to Ayal et al., which is assigned to the assignee of the present application and is incorporated herein by reference, describes apparatus for applying current to a nerve, including a housing, adapted to be placed in a vicinity of the nerve, and at least one cathode and at least one anode, fixed to the housing. The apparatus further includes two or more passive electrodes, fixed to the housing, and a conducting element, which electrically couples the passive electrodes to one another.

The following patents, which are incorporated herein by reference, may be of interest:
U.S. Pat. No. 6,684,105 to Cohen et al.
U.S. Pat. No. 5,423,872 to Cigaina
U.S. Pat. No. 4,573,481 to Bullara
U.S. Pat. No. 6,230,061 to Hartung
U.S. Pat. No. 5,282,468 to Klepinski
U.S. Pat. No. 5,487,756 to Kallesoe et al.
U.S. Pat. No. 5,634,462 to Tyler et al.
U.S. Pat. No. 6,456,866 to Tyler et al.
U.S. Pat. No. 4,602,624 to Naples et al.
U.S. Pat. No. 6,600,956 to Maschino et al.
U.S. Pat. No. 5,199,430 to Fang et al.
U.S. Pat. No. 5,824,027 Hoffer et al.

The following articles, which are incorporated herein by reference, may be of interest:
Naples G G et al., "A spiral nerve cuff electrode for peripheral nerve stimulation," by IEEE Transactions on Biomedical Engineering, 35(11) (1988)
Deurloo K E et al., "Transverse tripolar stimulation of peripheral nerve: a modelling study of spatial selectivity," Med Biol Eng Comput, 36(1):66-74 (1998)
Tarver W B et al., "Clinical experience with a helical bipolar stimulating lead," Pace, Vol. 15, October, Part II (1992)
Fitzpatrick et al., "A nerve cuff design for the selective activation and blocking of myelinated nerve fibers," Ann. Conf. of the IEEE Eng. in Medicine and Biology Soc, 13(2), 906 (1991)
Baratta R et al., "Orderly stimulation of skeletal muscle motor units with tripolar nerve cuff electrode," IEEE Transactions on Biomedical Engineering, 36(8):836-43 (1989)

SUMMARY OF THE INVENTION

In some embodiments of the present invention, a nerve stimulation and cardiac sensing system comprises at least one electrode device, which is applied to a nerve of a subject, such as a vagus nerve, at a location neither within nor in contact with a heart of the subject. The electrode device comprises one or more device first electrode contact surfaces that are configured to be placed in electrical contact with the nerve. The system further comprises a control unit, and at least one second sensing electrode contact surface which is not directly mechanically coupled to the electrode device, and which is configured to be positioned in the subject's body elsewhere than in the subject's heart, optionally at a location neither within nor in contact with the heart. The control unit uses the second sensing electrode contact surface and at least one of the device first electrode contact surfaces to sense a signal indicative of a parameter of a cardiac cycle of subject, such as one or more components of an electrocardiogram (ECG) of a heart of the subject. The control unit is typically configured to apply stimulation to the nerve, and/or configure the applied stimulation, at least in part responsively to the sensed cardiac parameter. For example, the control unit may configure the stimulation to regulate a heart rate of the subject. For some applications, the second sensing electrode contact surface is directly mechanically coupled to the control unit, while for other applications, the second sensing electrode contact surface is directly mechanically coupled to a lead that couples the control unit to the electrode device.

In some embodiments of the present invention, in addition to comprising a plurality of stimulating electrode contact surfaces within the electrode device, the electrode device comprises one or more external sensing electrode contact surfaces, which are fixed to an outer surface of the device. The control unit uses the external sensing electrode contact surfaces to sense a signal indicative of a parameter of a cardiac cycle of subject. In order to sense this property, the electrode device is typically configured to be implanted in a vicinity of a blood vessel of the subject. For some applications, the electrode device is implanted around a cervical vagus nerve in a vicinity of the carotid artery or the jugular vein. The control unit is typically configured to apply stimulation to the nerve, and/or configure the applied stimulation, at least in part responsively to the sensed cardiac parameter. For example, the control unit may configure the stimulation to regulate a heart rate of the subject.

As used in the present application, including in the claims, an "electrode" is an electrically conductive contact surface that is not electrically insulated, which is typically coupled to at least one other element by one or more leads, and an "electrode device" is a device which is configured to be positioned in a vicinity of a nerve, and which comprises at least one electrode that is configured to make electrical contact with tissue, in order to apply electrical stimulation to the tissue and/or sense an electrical property of the tissue.

There is therefore provided, in accordance with an embodiment of the present invention, apparatus for application to a nerve of a subject, the apparatus including an electrode device, which includes:

a housing, which is configured to be placed at least partially around the nerve, so as to define an outer surface of the electrode device and an inner surface that faces the nerve;

one or more first electrode contact surfaces, fixed to the inner surface of the housing; and one or more second electrode contact surfaces, fixed to the outer surface of the housing.

In an embodiment, the apparatus further includes a control unit, which includes:

a driving unit, which is configured to drive the first electrode contact surfaces to apply electrical stimulation to the nerve;

a sensing unit, which is configured to sense an electrical signal, using at least one of the second electrode contact surfaces; and an analysis unit, which is configured to analyze the signal to identify a parameter of a cardiac cycle of the subject.

For some applications, the nerve is the vagus nerve, and the electrode device is configured to be implanted such that the second electrode contact surfaces are in a vicinity of a blood vessel selected from the group consisting of: a carotid artery and a jugular vein.

There is further provided, in accordance with an embodiment of the present invention, apparatus including:

an electrode device, which includes one or more device first electrode contact surfaces, and which is configured to be placed in a vicinity of a nerve of a subject at a first location neither within nor in contact with a heart of the subject;

at least one second electrode contact surface, which is not directly mechanically coupled to the electrode device, and which is configured to be positioned in a body of the subject at a second location neither within nor in contact with the heart; and a control unit, which includes:

a sensing unit, which is configured to sense, using at least one of the device first electrode contact surfaces and the at least one second electrode contact surface, an electrical signal; and an analysis unit, which is configured to analyze the signal to identify a parameter of a cardiac cycle of the subject.

For some applications, the at least one second electrode contact surface is directly mechanically coupled to the control unit. For some applications, the control unit includes a metal can having an outer conductive surface, at least a portion of which serves as the at least one second electrode contact surface.

For some applications, the electrode device includes a housing, which is configured to be placed at least partially around the nerve, so as to define an outer surface of the electrode device and an inner surface that faces the nerve, and the one or more device first electrode contact surfaces are fixed to the inner surface of the housing. For some applications, the electrode device includes a housing, which is configured to be placed at least partially around the nerve, so as to define an outer surface of the electrode device and an inner surface that faces the nerve, and the one or more device first electrode contact surfaces are fixed to the outer surface of the housing.

For some applications, the nerve is the vagus nerve, and the electrode device is configured to be placed in the vicinity of the vagus nerve.

For some applications, the electrode device is configured to be placed at least partially around the nerve.

In an embodiment, the control unit includes a driving unit, which is configured to drive at least some of the device first electrode contact surfaces to apply electrical stimulation to the nerve, and configure the stimulation responsively to the parameter of the cardiac cycle. For some applications, the device first electrode contact surfaces include one or more stimulating device first electrode contact surfaces and one or more sensing stimulating device first electrode contact surfaces, the driving unit is configured to drive the stimulating device first electrode contact surfaces, and not the sensing stimulating device first electrode contact surfaces, to apply the stimulation, and the sensing unit is configured to sense the electrical signal using the sensing device first electrode contact surfaces, and not using the stimulating device first electrode contact surfaces. For some applications, the parameter of the cardiac cycle is indicative of ventricular contraction, and the driving unit is configured to drive the at least some of the device first electrode contact surfaces to apply the stimulation during at least one heart beat after a delay from the ventricular contraction, the delay having a duration of at least 20 ms.

In an embodiment, the apparatus further includes at least one lead coupled to the control unit, and the at least one second electrode contact surface is directly mechanically coupled to the lead. For some applications, the at least one lead couples the electrode device to the control unit, and the at least one second electrode contact surface is directly mechanically coupled to the lead at a position between the electrode device and the control unit.

There is still further provided, in accordance with an embodiment of the present invention, apparatus including:

an electrode device, which is configured to be placed in a vicinity of a nerve of a subject at a location neither within nor in contact with a heart of the subject;

a control unit;

at least one lead that couples the electrode device to the control unit;

at least one first electrode contact surface that is directly mechanically coupled to the lead at a location between the electrode device and the control unit; and at least one second electrode contact surface that is directly mechanically coupled to the control unit, and the control unit includes:

a sensing unit, which is configured to sense, using the at least one first electrode contact surface and the at least one second electrode contact surface, an electrical signal; and an analysis unit, which is configured to analyze the signal to identify a parameter of a cardiac cycle of the subject.

For some applications, the control unit includes a metal can having an outer conductive surface, at least a portion of which serves as the at least one second electrode contact surface.

For some applications, the electrode device is configured to be placed at least partially around the nerve.

There is additionally provided, in accordance with an embodiment of the present invention, a method including:

placing an electrode device in a vicinity of a nerve and in a vicinity of a blood vessel of a subject, at a location neither within nor in contact with a heart of the subject;

applying electrical stimulation to the nerve using the electrode device; and sensing, using the electrode device, a signal from the blood vessel indicative of a parameter of a cardiac cycle of the subject.

For some applications, the nerve is cervical vagus nerve, the blood vessel is selected from the group consisting of: a carotid artery and a jugular vein, and placing includes placing the electrode device in the vicinity of the cervical vagus nerve and in the vicinity of the selected blood vessel.

There is yet additionally provided, in accordance with an embodiment of the present invention, a method including:

placing an electrode device in a vicinity of a nerve of a subject at a first location neither within nor in contact with a heart of the subject; and sensing, between the electrode device and a second location within a body of the subject neither within nor in contact with the heart, a signal indicative of a parameter of a cardiac cycle of the subject.

There is also provided, in accordance with an embodiment of the present invention, a method including:

placing an electrode device in a vicinity of a nerve of a subject at location neither within nor in contact with a heart of the subject; and using an implanted control unit coupled to the electrode device by at least one lead, sensing, between the control unit and a location along the lead, a signal indicative of a parameter of a cardiac cycle of the subject.

The present invention will be more fully understood from the following detailed description of embodiments thereof, taken together with the drawings, in which:

DETAILED DESCRIPTION OF EMBODIMENTS

Figure 1:
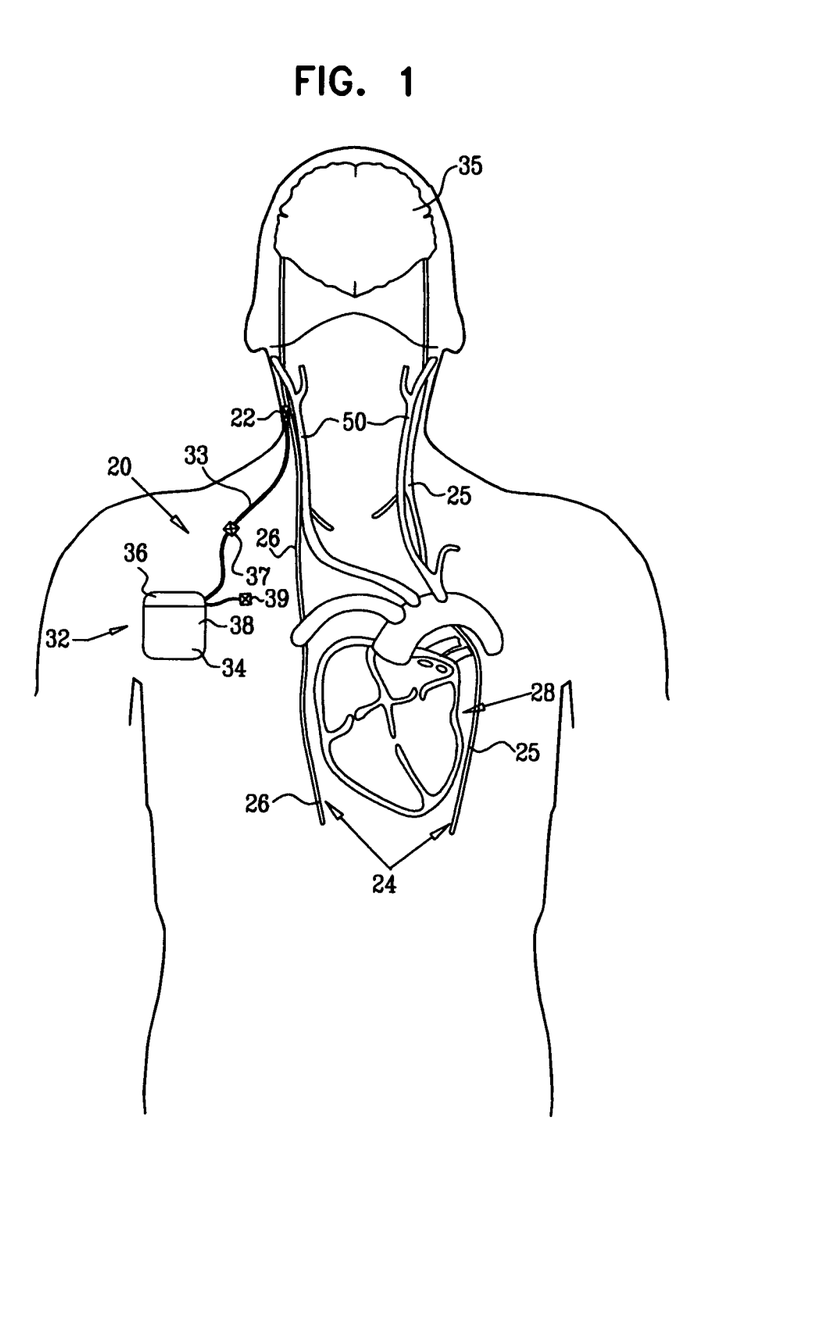
FIG. 1 is a schematic illustration of a nerve stimulation and cardiac sensing system, in accordance with an embodiment of the present invention.

FIG. 1 is a schematic illustration of a nerve stimulation and cardiac sensing system 20, in accordance with an embodiment of the present invention. System 20 comprises at least one electrode device 22, which is configured to be positioned in a vicinity of a nerve of a subject, at a location neither within nor in contact with a heart 28 of the subject (i.e., neither within the heart nor in contact with any tissue of the heart, including tissue of an external surface of the heart). For example, the nerve may be a vagus nerve 24 (either a left vagus nerve 25 or a right vagus nerve 26), which innervates heart 28. For some applications, the electrode device is configured to be placed at least partially around the nerve. For some applications, electrode device 22 is applied to a cervical vagus nerve of the subject, as shown in FIG. 1. Electrode device 22 comprises one or more nerve-facing electrode contact surfaces that are configured to be placed in electrical contact with the nerve, such as using techniques described hereinbelow with reference to FIG. 3, described in the references incorporated herein by reference hereinbelow or in the Background section, and/or known in the art.

Figure 3:
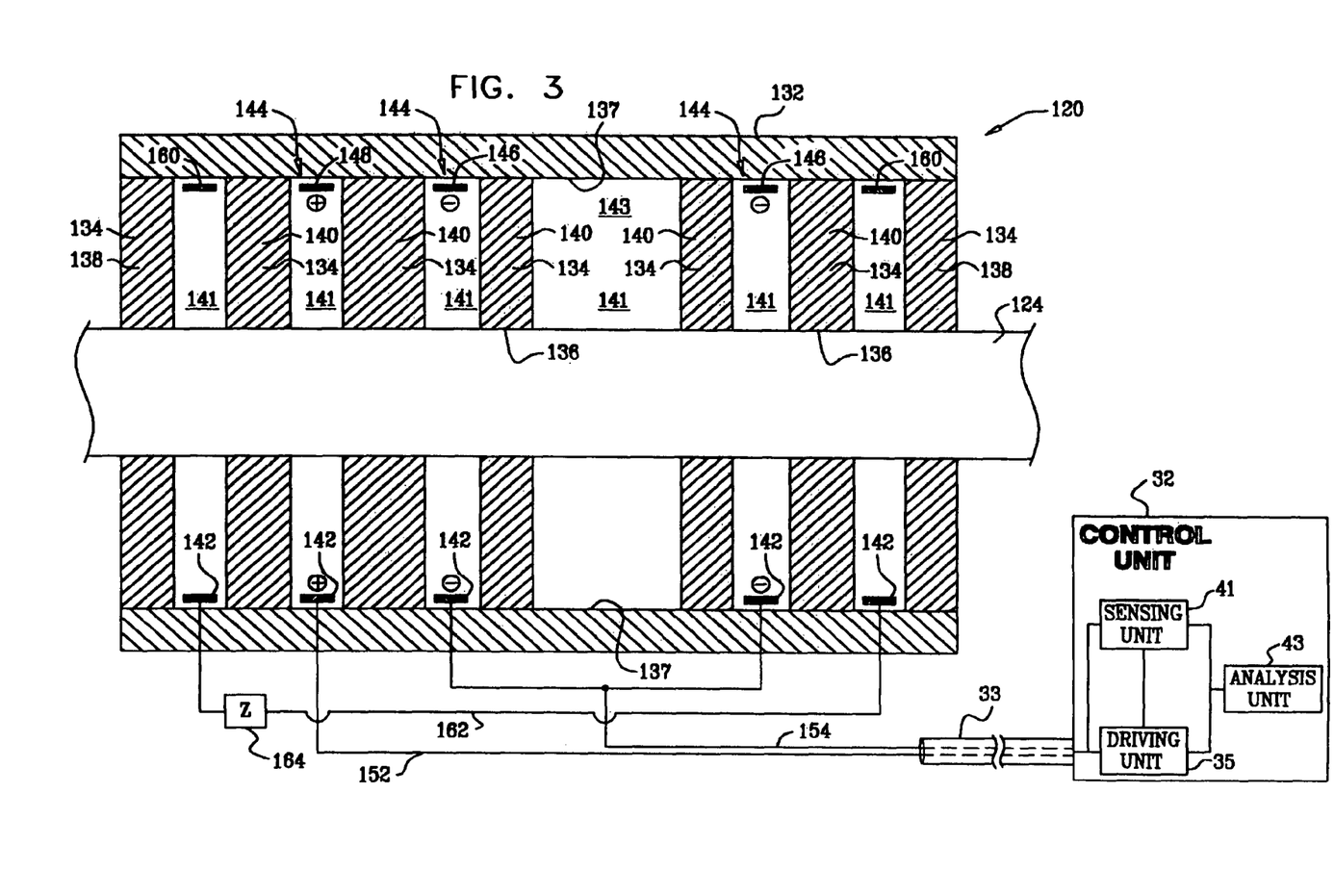
FIG. 3 is a schematic, cross-sectional illustration of an electrode cuff for applying current to a nerve, in accordance with an embodiment of the present invention.

System 20 further comprises a control unit 32, which typically communicates with electrode device 22 over at least one lead 33, which comprises one or more elongated conducting elements, such as wires, and an electrically insulating outer layer, comprising, for example, polyurethane or a similar insulation material. Control unit 32 typically comprises an implantable can, which houses circuitry of the control unit. The can typically comprises a metal body 34 and a non-metallic header 36, which provides one or more connection points for lead 33. For some applications, control unit 32 comprises one or more of a driving unit 35, a sensing unit 41, and an analysis unit 43, as shown in FIG. 3 and described hereinbelow. For some applications, control unit 32 further comprises an output unit, which is configured to generate an output signal, as described hereinbelow.

In an embodiment of the present invention, control unit 32 comprises at least one first sensing electrode contact surface 38. For some applications, all or a portion of the outer surface of metal body 34 of the can serves as first sensing electrode contact surface 38. Alternatively, the control unit comprises a separate conductive element that serves as first sensing electrode contact surface 38, which is directly mechanically coupled to the outer surface of the can. Alternatively or additionally, system 20 comprises a second sensing electrode contact surface 37 directly mechanically coupled to lead 33 at a point along the lead between control unit 32 and electrode device 22. Still further alternatively or additionally, system 20 comprises a third sensing electrode contact surface 39, positioned at a location other than in direct mechanical contact with electrode device 22 or lead 33, and which is typically configured to positioned in the subject's body elsewhere than in heart 28 (e.g., at a location neither within nor in contact with the heart, or at a location in a vicinity of the heart, such as in contact with an external surface of the heart). For example, as shown in FIG. 1, third sensing electrode contact surface 39 may be coupled to another lead that is coupled to control unit 32.

In order to sense a signal indicative of a parameter of a cardiac cycle of the subject, such as one or more components of an electrocardiogram (ECG) of heart 28, sensing unit 41 of control unit 32 uses two or more of the following electrodes contact surface:

first sensing electrode contact surface 38;
second sensing electrode contact surface 37;
third sensing electrode contact surface 39;
at least one of the nerve-facing electrode contact surfaces of electrode device 22, such as at least one of nerve-facing electrode contact surfaces 142 described hereinbelow with reference to FIG. 3;
at least one of external sensing electrode contact surfaces 44 of the electrode device, described hereinbelow with reference to FIG. 2; and
at least one blood-vessel-facing electrode contact surface of a blood vessel cuff configured to be placed in a vicinity of or around a blood vessel of the subject, such as a jugular vein or a carotid artery, such as described hereinbelow with reference to FIG. 4.

For example, the sensing unit of the control unit may sense the cardiac signal using one of the following combinations of electrode contact surfaces:

first sensing electrode contact surface 38 and at least one of the nerve-facing electrode contact surfaces of electrode device 22;
first sensing electrode contact surface 38 and second sensing electrode contact surface 37;
first sensing electrode contact surface 38 and at least one of external sensing electrode contact surfaces 44;
first sensing electrode contact surface 38 and third sensing electrode contact surface 39;
second sensing electrode contact surface 37 and at least one of the nerve-facing electrode contact surfaces of electrode device 22;
second sensing electrode contact surface 37 and at least one of external sensing electrode contact surfaces 44;

third sensing electrode contact surface 39 and at least one of the nerve-facing electrode contact surfaces of electrode device 22;

third sensing electrode contact surface 39 and at least one of external sensing electrode contact surfaces 44;

at least two of external sensing electrode contact surfaces 44;

at least one of external sensing electrode contact surfaces 44 and at least of the nerve-facing electrode contact surfaces of electrode device 22; or at least one of the blood-vessel-facing electrode contact surface of the blood vessel cuff.

Sensing unit 41 of control unit 32 senses an electrical signal, and analysis unit 43 of control unit 32 analyzes the sensed signal to identify the parameter of the cardiac cycle. For example, the parameter may be an R-R interval, an average heart rate, the timing of an A wave, or the timing of an R wave. For some applications, the output unit of the control unit is configured to generate an output signal responsively to the parameter of the cardiac cycle.

For some applications, the sensing unit of the control unit senses the cardiac signal using at least one first blood-vessel-facing electrode contact surface of a first blood vessel cuff, and at least one second blood-vessel-facing electrode contact surface of a second blood vessel cuff. For example, the blood vessel cuffs may use techniques described hereinbelow with reference to FIG. 4. Alternatively, the two electrode contact surfaces may be configured to be placed in a vicinity of the blood vessel without being placed around at least a portion of the blood vessel.

Driving unit 35 of control unit 32 is typically configured to apply stimulation to the nerve, and/or configure the applied stimulation, at least in part responsively to the sensed cardiac parameter. For example, the driving unit of the control unit may configure the stimulation to regulate a heart rate of the subject, using heart rate regulation techniques described in the art, and/or in the applications incorporated by reference hereinbelow or in the Background section. For example, the parameter may be a R-R interval of the ECG, and the control unit may cease or reduce a strength of the applied stimulation when the R-R interval exceeds a threshold value. For some applications, the cardiac parameter is indicative of ventricular contraction, and the driving unit of the control unit is configured to apply the stimulation during at least one heart beat after a delay from the ventricular contraction. For example, the delay may have a duration of at least 10 ms, such as at least 20 ms or at least 30 ms.

For some applications, electrode device 22 comprises one or more stimulating nerve-facing electrode contact surfaces and one or more sensing nerve-facing electrode contact surfaces. Driving unit 35 of control unit 32 is configured to drive the stimulating nerve-facing electrode contact surfaces, and not the sensing nerve-facing electrode contact surfaces, to apply the stimulation to the nerve. Sensing unit 41 of control unit 32 is configured to sense the cardiac signal using the sensing nerve-facing electrode contact surfaces, and not using the stimulating nerve-facing electrode contact surfaces (and, optionally, one or more additional sensing electrodes of system 20, as described hereinabove). This technique generally allows sensing unit 41 to begin sensing the cardiac signal soon after the conclusion of the application of stimulation, without waiting for the stimulating nerve-facing electrode contact surfaces to discharge.

Figure 2:
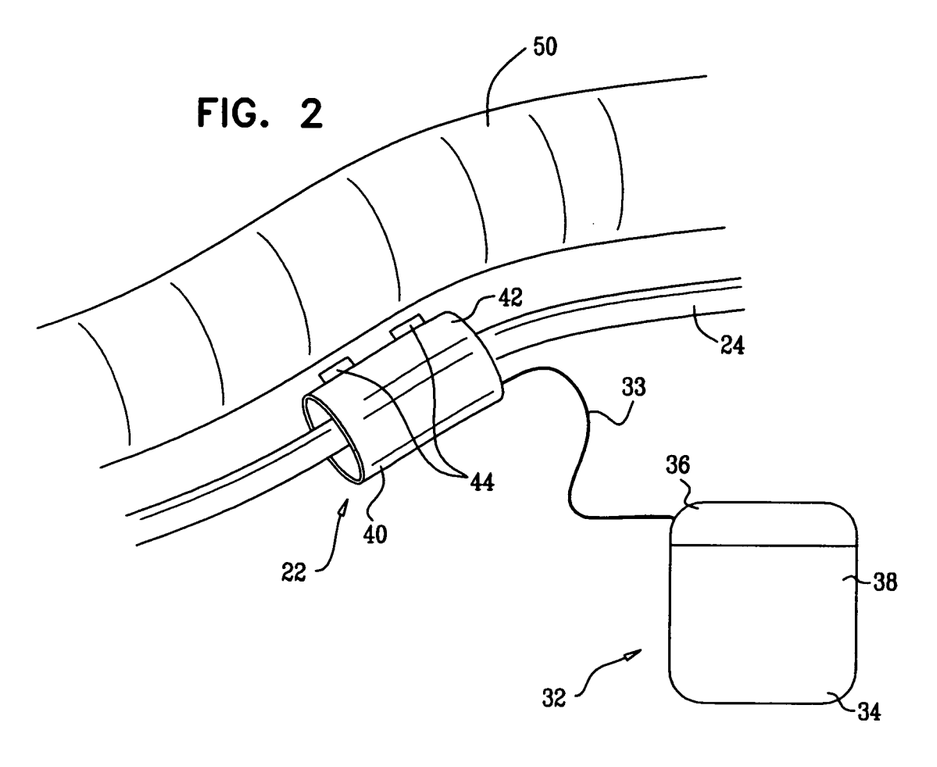
FIG. 2 is a schematic illustration of an electrode device, in accordance with an embodiment of the present invention.

FIG. 2 is a schematic illustration of electrode device 22, in accordance with an embodiment of the present invention. In this embodiment, electrode device 22 comprises a housing 40 which defines an outer surface 42 of the device when the device is placed at least partially around vagus nerve 24, or another nerve of the subject, e.g., an autonomic nerve (either parasympathetic or sympathetic). Typically, electrode device 22 comprises an electrode cuff. Except as described below, electrode device 22 may be configured in accordance with any of the embodiments described hereinbelow, in the patent applications incorporated by reference hereinbelow or in the Background section, or otherwise as known in the art of electrode cuffs.

In addition to comprising a plurality of nerve-facing stimulating electrode contact surfaces within the electrode device (for example, nerve-facing electrode contact surfaces 142, described hereinbelow with reference to FIG. 3), electrode device 22 comprises one or more external sensing electrode contact surfaces 44, fixed to outer surface 42 of housing 40. Sensing unit 41 of control unit 32 uses external sensing electrode contact surfaces 44 to sense a signal indicative of a parameter of a cardiac cycle of the subject, such as one or more components of an ECG of heart 28. For some applications, in order to sense this property, the electrode device is configured to be implanted in a vicinity (e.g., within 10 mm, such as within 2 mm) of a blood vessel 50 of the subject, such as an artery, e.g., a carotid artery or a jugular vein. Alternatively or additionally, the electrode device is implanted within a distance of the blood vessel that is no more than twice a distance between two of external sensing electrode contact surfaces 44. For some applications, the electrode device is implanted around a cervical vagus nerve in a vicinity of the carotid artery or the jugular vein. Alternatively, the electrode device is not configured to be placed in a vicinity of a blood vessel.

Driving unit 35 of control unit 32 is typically configured to apply stimulation to the nerve, and/or configure the applied stimulation, at least in part responsively to the sensed cardiac parameter. For example, the control unit may configure the stimulation to regulate a heart rate of the subject, as described hereinabove with reference to FIG. 1.

For some application, sensing unit 41 of control unit 32 senses the cardiac property using one or more sensing electrode contact surfaces 44 and one or more of the electrode contact surfaces within the electrode device. Alternatively or additionally, the sensing unit of the control unit senses the cardiac property using one or more sensing electrode contact surfaces 44 and sensing electrode contact surface 38, described hereinabove with reference to FIG. 1.

FIG. 3 is a schematic, cross-sectional illustration of an electrode cuff 120 for applying current to a nerve 124, in accordance with an embodiment of the present invention. Electrode cuff 120 comprises a housing 132 which defines an outer surface of the cuff when the cuff is placed at least partially around nerve 124. Housing 132 typically comprises an elastic, electrically-insulating material such as silicone or polyurethane, which may have, for example, a Shore A of between about 35 and about 70, such as about 40.

Electrode cuff 20 further comprises a plurality of insulating elements 134 that are arranged at respective positions along the housing, and are typically fixed to an inner surface 137 of housing 132 that faces nerve 124 when the electrode cuff is placed at least partially around the nerve. Insulating elements 134 typically comprise an elastic, electrically-insulating material such as silicone or silicone copolymer, which, for some applications, is softer than that of housing 132, for example, a Shore A of between about 10 and about 30, such as about 10. Electrode cuff 120 is typically configured such that, after placement of the cuff around the nerve, respective contact surfaces 136 of insulating elements 134 come in physical contact with the nerve, or substantially in physical contact with the nerve, e.g., are less than about 0.5 mm from the surface of the nerve. For some applications, a length that at least one of insulating elements 134 protrudes from housing 132 toward nerve 124 is at least 0.5 mm, such as at least 1 mm. For some applications, insulating elements 134 and housing 132 are constructed as separate elements that are coupled to one another, while for other applications, the insulating elements and housing are constructed as a single integrated element that is shaped to define the insulating elements and housing.

Insulating elements 134 typically comprise one or more (such as exactly two) end insulating elements 138 arranged at or near respective ends of the cuff, and two or more internal insulating elements 140 arranged at respective positions along the cuff between the end insulating elements. End insulating elements 138 extend along nerve 124 in order to electrically isolate a portion of the nerve within electrode cuff 120 from a portion of the nerve outside the electrode cuff.

Inner surface 137 of housing 132 and pairs of insulating elements 134 define a respective cavities 141 along the housing. (It is noted that some pairs of the insulating elements may not define a cavity, such as if two or more of the insulating elements are arranged in contact with one another.)

Electrode cuff 120 comprises a plurality of nerve-facing electrode contact surfaces 142, fixed within housing 132 in respective cavities 141 defined by respective pairs insulating elements 134 and inner surface 137 of housing 132. At least one of cavities 141 defined by a pair of the insulating elements does not have an electrode contact surface positioned therein. For example, in the embodiment shown in FIG. 3, the insulating elements define six cavities 141, a fourth one 143 of which (counting from the left in the figure) does not have an electrode contact surface positioned therein. For some applications, at least two, such as least three, of the cavities do not have electrode contact surfaces positioned therein. Nerve-facing electrode contact surfaces 142 are typically fixed to inner surface 137 of housing 132.

For some applications, at least one of the empty cavities has a length along the cuff of at least 0.5 mm, such as at least 0.7 mm, e.g., at least 1.4 mm or at least 2 mm, and/or no more than 5 mm, e.g., no more than 2 mm. For some applications, a length along the cuff of one of the empty cavities is between about 0.5 and about 5 times a length of one of the cavities that has an electrode contact surface therein, such as between about 1 and about 2 times the length.

For some applications, at least one of the empty cavities is directly adjacent along the cuff to two cavities containing an anode electrode contact surface and a cathode electrode contact surface, respectively. For some applications, at least one of the empty cavities is directly adjacent along the cuff to two cavities containing two respective anode electrode contact surfaces, or to two cavities containing two respective cathode electrode contact surfaces. Alternatively, at least one of the two endmost cavities is empty, e.g., one side of at least one of the empty cavities is defined by one of end insulating elements 138.

Internal insulating elements 140 are arranged so as to electrically separate nerve-facing electrode contact surfaces 142, and to guide current from one of the electrode contact surfaces towards the nerve prior to being taken up by another one of the electrode contact surfaces. Typically (as shown), insulating elements 134 are closer to nerve 124 than are the electrode contact surfaces, i.e., the electrode contact surfaces are recessed within the cavities. Alternatively (not shown), insulating elements 134 are generally flush with the faces of the electrode contact surfaces, such that the inner surfaces of insulating elements and the conductive surfaces of the electrode contact surface are equidistant from the nerve.

Nerve-facing electrode contact surfaces 142 comprise at least one active, i.e., stimulating and/or sensing, electrode contact surface 144, such as at least one cathode electrode contact surface 146 and at least one anode electrode contact surface 148. Active electrode contact surfaces 144 are coupled to control unit 32 by conducting elements 152 and 154 of lead 33. For some applications, active electrode configurations and/or stimulation techniques are used which are described in one or more of the patent applications incorporated by reference hereinbelow. For some applications, two or more of the active electrode contact surfaces are shorted to one another inside or outside of the cuff, such as shown for cathode electrode contact surfaces 146 in FIG. 3.

In an embodiment of the present invention, electrode cuff 120 further comprises two or more passive electrode contact surfaces 160, fixed within housing 132, and a conducting element 162, typically a wire, which electrically couples the passive electrode contact surfaces to one another. A "passive electrode contact surface," as used in the present application including the claims, is an electrode contact surface that is electrically "device-coupled" to neither (a) any circuitry that is electrically device-coupled to any of the cathode electrode contact surfaces or anode electrode contact surfaces, nor (b) an energy source. "Device-coupled" means coupled, directly or indirectly, by components of a device, and excludes coupling via tissue of a subject. (It is noted that the passive electrode contact surfaces may be passive because of a software-controlled setting of the electrode assembly, and that the software may intermittently change the setting such that these electrode contact surfaces are not passive.) To "passively electrically couple," as used in the present application including the claims, means to couple using at least one passive electrode contact surface and no non-passive electrode contact surfaces. Passive electrode contact surfaces 160 and conducting element 162 create an additional electrical path for the current, such as an additional path for the current that would otherwise leak outside electrode cuff 120 and travel around the outside of the housing through tissue of the subject. For some applications, conducting element 162 comprises at least one passive element 164, such as a resistor, capacitor, and/or inductor. In this embodiment, end insulating elements 138 help direct any current that leaks from active electrode contact surfaces 144 through the electrical path created by passive electrode contact surfaces 160 and conducting element 162. For some applications, active electrode contact surfaces 144 are positioned within housing 132 longitudinally between the two or more passive electrode contact surfaces 160 (as shown in FIG. 3). Alternatively, at least one of the passive electrode contact surfaces is positioned between the at least one cathode electrode contact surface and the at least one anode electrode contact surface (configuration not shown).

In an embodiment of the present invention, electrode cuff 120 comprises one or more passive electrode contact surfaces 160 which are not electrically device-coupled to one another. For some applications, the electrode cuff comprises exactly one passive electrode contact surface 160. A separate conducting element, typically a wire, is coupled to each passive electrode contact surface at a first end of the conducting element. The second end of the conducting element terminates at a relatively-remote location in the body of the subject that is at a distance of at least 1 cm, e.g., at least 2 or 3 cm, from electrode cuff 120. The remote location in the body thus serves as a ground for the passive electrode contact surface. For some applications, an electrode contact surface is coupled to the remote end of the conducting element, so as to increase electrical contact with tissue at the remote location.

For some applications, housing 132 has a length of between about 10 and about 14 mm, e.g., about 12.1 mm; an outer radius of between about 4 and about 8 mm, e.g., about 5.9 mm; and an inner radius of between about 3 and about 6 mm, e.g., about 4.5 mm. For some applications, insulating elements 134 have an outer radius of between about 3 and about 6 mm, e.g., about 4.5 mm (the outer radius of the insulating elements is typically equal to the inner radius of the housing), and an inner radius of between about 2 and about 3.5 mm. For some applications in which cuff 120 comprises exactly two end insulating elements 138 and exactly five internal insulating elements 140, respective edges of insulating elements 134 are positioned within cuff 32 at the following distances from one end of the cuff: 0.0 mm, between 1.3 and 1.7 mm (e.g., 1.5 mm), between 2.7 and 3.3 mm (e.g., 3.0 mm), between 5.1 and 6.3 mm (e.g., 5.7 mm), between 7.1 and 8.7 mm (e.g., 7.9 mm), between 8.5 and 10.3 mm (e.g., 9.4 mm), and between 10.2 and 12.4 mm (e.g., 11.3 mm), and the insulating elements having the following respective widths: between 0.7 and 0.9 mm (e.g., 0.8 mm), between 0.7 and 0.9 mm (e.g., 0.8 mm), between 1.4 and 1.8 mm (e.g., 1.6 mm), between 0.7 and 0.9 mm (e.g., 0.8 mm), between 0.7 and 0.9 mm (e.g., 0.8 mm), between 1.1 and 1.3 mm (e.g., 1.2 mm), and between 0.7 and 0.9 mm (e.g., 0.8 mm). For some applications, electrode contact surfaces 142 comprise Pt/Ir. For some applications, as shown in FIG. 3, electrode contact surfaces 142 are shaped as rings (e.g., reference numeral 160 and leftmost reference numeral 142 in FIG. 3 refer to a single ring electrode contact surface). The rings may have an outer radius that equals, or is slightly greater or less than, the inner radius of housing 132.

In an embodiment of the present invention, at least some of the electrode contact surfaces do not comprise ring electrode contact surfaces. Instead, each of at least one of non-empty cavities 141 has fixed therein a plurality of electrode contact surfaces positioned at least partially circumferentially around a central axis of the cuff. In other words, electrode contact surfaces 142 are first electrode contact surfaces 142, fixed within housing 132 in respective cavities 141, and cuff 120 comprises at least one second electrode contact surface 142, fixed within housing 132 in one of the cavities 141 in which one of the first electrode contact surfaces 142 is fixed. For some applications, the plurality of electrode contact surfaces within a single cavity are circumferentially separated from one another by one or more circumferentially arranged insulating elements.

In an embodiment of the present invention, at least one of the one or more of cavities 141 which are empty in the embodiments described hereinabove, instead has fixed therein one or more electrode contact surfaces that are not electrically device-coupled (as defined hereinabove) to any elements of the device outside of the cavity. These electrode contact surfaces thus do not serve the normal function of electrode contact surfaces in an electrode cuff, i.e., conducting current to and/or from tissue.

In some embodiments of the present invention in which nerve 124 is vagus nerve 24, electrode cuff 120 is configured to be placed at least partially around the vagus nerve such that anode electrode contact surface 148 is more proximal to a brain 150 of the subject (FIG. 1) than are cathode electrode contact surfaces 146.

For some applications, electrode cuff 120 is configured to selectively stimulate fibers of the nerve having certain diameters, such as by using techniques described in one or more of the patent applications incorporated by reference hereinbelow. For example, control unit 32 may comprise a driving unit, which is configured to drive cathode electrode contact surface 146 to apply to nerve 124 a stimulating current, which is capable of inducing action potentials in a first set and a second set of nerve fibers of the nerve, and drive anode electrode contact surface 148 to apply to the nerve an inhibiting current, which is capable of inhibiting the induced action potentials traveling in the second set of nerve fibers, the nerve fibers in the second set having generally larger diameters than the nerve fibers in the first set.

For some applications, electrode cuff 120 is configured to apply unidirectional stimulation to the nerve, such as by using techniques described in one or more of the patent applications incorporated by reference hereinbelow. For example, control unit 32 may comprise a driving unit, which is configured to drive anode electrode contact surface 148 to apply an inhibiting current capable of inhibiting device-induced action potentials traveling in a non-therapeutic direction in nerve 124. For some applications, electrode cuff 120 comprises primary and secondary anode electrode contact surfaces, the primary anode electrode contact surface located between the secondary anode electrode contact surface and the cathode electrode contact surface. The secondary anode electrode contact surface is typically adapted to apply a current with an amplitude less than about one half an amplitude of a current applied by the primary anode electrode contact surface.

In an embodiment of the present invention, techniques described herein are practiced in combination with techniques described with reference to FIGS. 2, 3, and/or 6 of U.S. patent application Ser. No. 11/280,884 to Ayal et al., filed Nov. 15, 2005, which published as US Patent Application Publication 2006/0106441, and which is assigned to the assignee of the present application and is incorporated herein by reference. For example:

for some applications, a closest distance between cathode electrode contact surfaces 146 (i.e., the distance between the respective cathode electrode contact surfaces' edges that are closest to one another) is equal to at least a radius R of nerve 124, e.g., at least 1.5 times the radius of the nerve, as described with reference to FIG. 2 of the '441 publication; and/or for some applications, end insulating elements 138 are elongated, as described with reference to FIG. 6 of the '441 publication.

Figure 4:
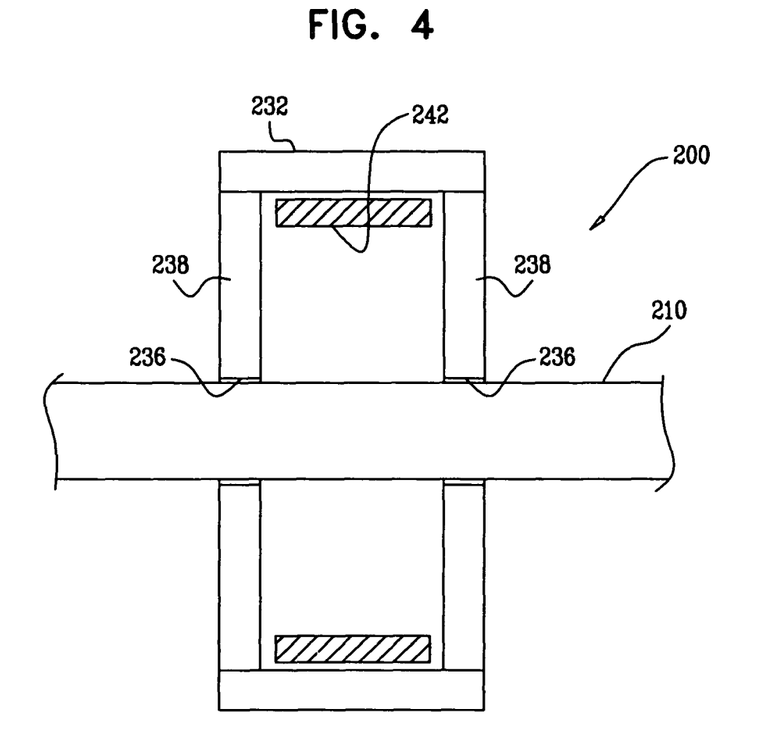
FIG. 4 is a schematic, cross-sectional illustration of an electrode cuff for sensing a cardiac signal at a blood vessel, in accordance with an embodiment of the present invention.

FIG. 4 is a schematic, cross-sectional illustration of an electrode cuff 200 for sensing a cardiac signal at a blood vessel 210, in accordance with an embodiment of the present invention. For example, blood vessel 210 may be a jugular vein or a carotid artery. Electrode cuff 200 comprises a housing 232 which defines an outer surface of the cuff when the cuff is placed at least partially around blood vessel 210. Housing 232 may comprise an elastic, electrically-insulating material such as silicone or polyurethane.

Electrode cuff 200 further comprises one or more (such as exactly two) end insulating elements 238 arranged at or near respective ends of the cuff, which are typically fixed to an inner surface of housing 232 that faces blood vessel 210 when the electrode cuff is placed at least partially around the blood vessel. Insulating elements 238 typically comprise an elastic, electrically-insulating material such as silicone or silicone copolymer, which, for some applications, is softer than that of housing 232.

Electrode cuff 200 comprises at least one blood-vessel-facing electrode contact surface 242 (such as exactly one electrode contact surface 242) fixed within housing 232. For some applications, electrode contact surface 242 is used for sensing an electrical signal, such as described hereinabove with reference to FIG. 1.

It is noted that although electrode cuffs 120 and 200 and their elements are generally shown in the figures and described herein in a cylindrical configuration, other geometrical configurations, such as non-rotationally symmetric configurations, are also suitable for applying the principles of the present invention. In particular, housings 132 or 232 of the electrode cuffs (and the electrode contact surfaces themselves) may form a complete circle around nerve 124 or blood vessel 210, or they may define an arc between approximately 0 and 90 degrees, between 90 and 180 degrees, between 180 and 350 degrees, or between 350 and 359 degrees around the nerve or blood vessel. For some applications, electrode cuff 120 or 200 comprise electrode contact surfaces that form rings around the nerve or blood vessel, such that housing 132 or 232 surrounds the electrode contact surfaces.

Figure 5:
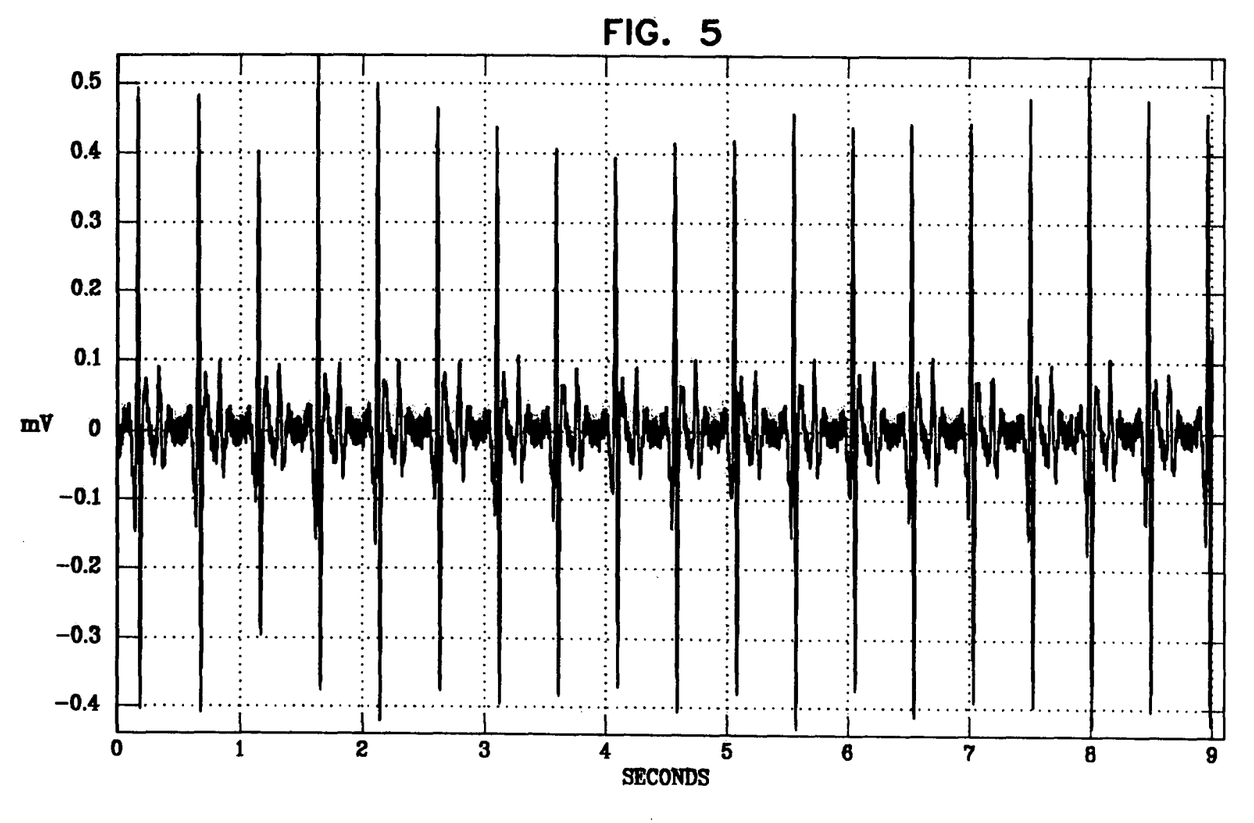
FIGS. 5-7 are graphs illustrating experimental results measured in accordance with respective embodiments of the present invention.
Figure 6:
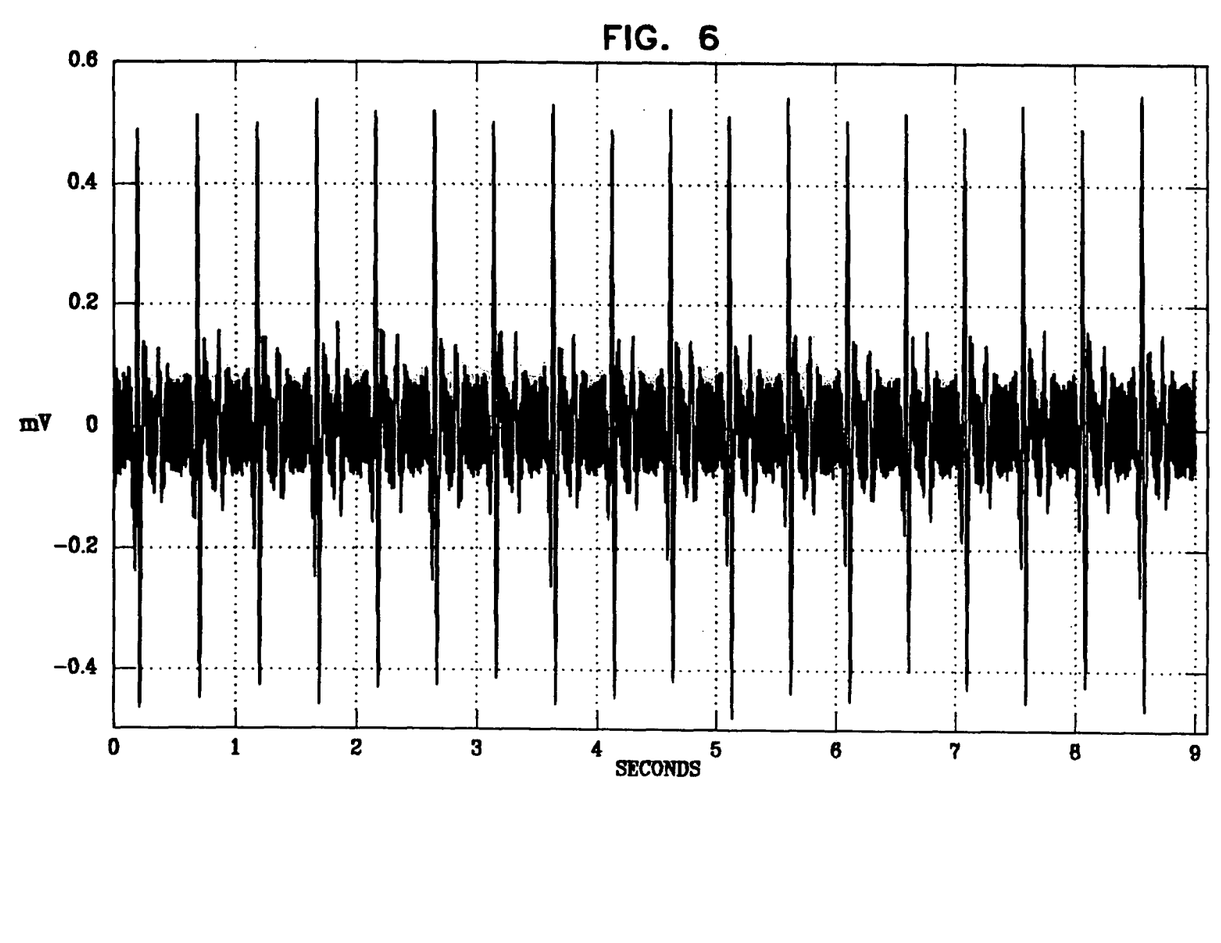
Figure 7:
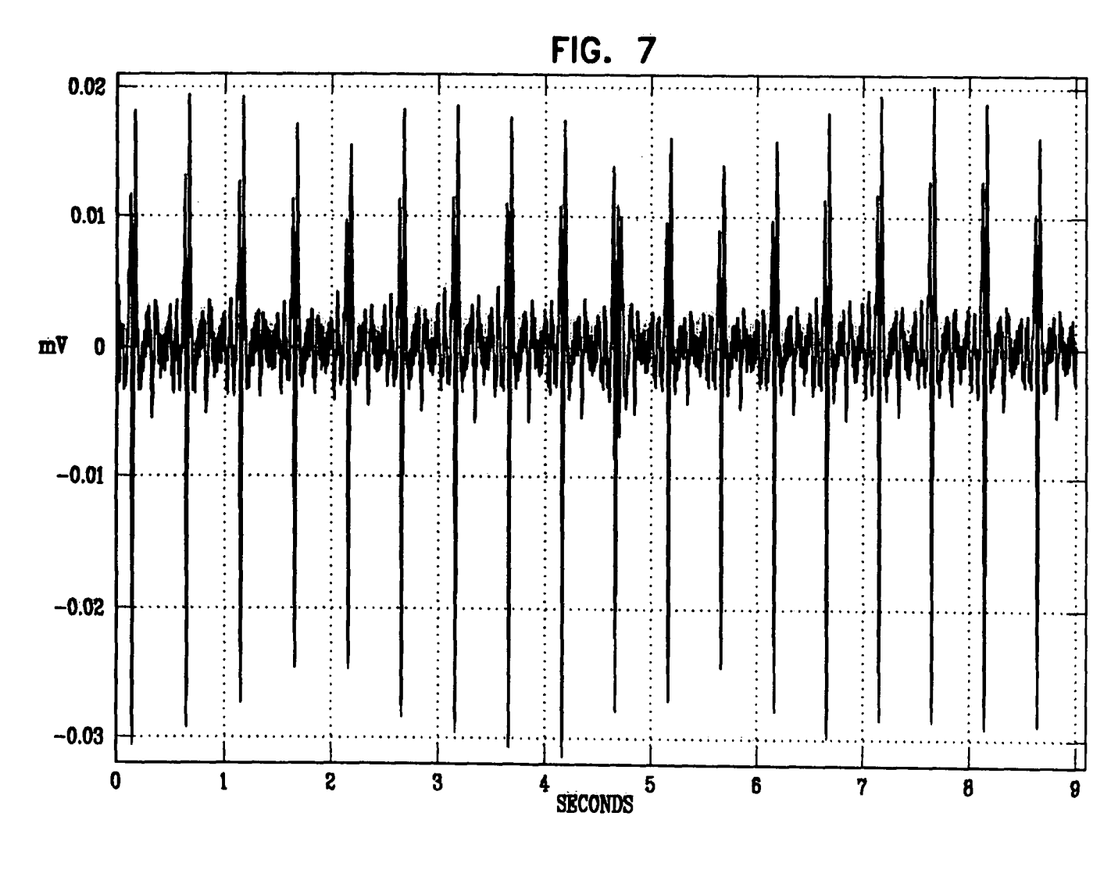

FIGS. 5-7 are graphs illustrating experimental results measured in accordance with respective embodiments of the present invention. These graphs show respective electrocardiograms measured in a single dog while under general anesthesia.

The electrocardiogram shown in FIG. 5 was measured between (a) a can implanted in the chest of the dog on the right thoracic side, over the pectoralis major muscle, inferior to the clavicle bone and (b) a cardiac pacemaker electrode lead placed at a cervical location, in proximity to the right cervical vagus nerve and the right jugular vein, approximately 30 cm from the can. This configuration was similar to the embodiment described hereinabove with reference to FIG. 1, in which the cardiac signal is sensed using (a) the outer surface of metal body 34 of the can serving as first sensing electrode contact surface 38, and (b) second sensing electrode contact surface 37. This configuration was also similar to the embodiment described hereinabove with reference to FIGS. 1 and 2, in which the cardiac signal is sensed using (a) the outer surface of metal body 34 of the can serving as first sensing electrode contact surface 38, and (b) external sensing electrode contact surface 44, described hereinabove with reference to FIG. 2, when not necessarily placed in the vicinity of blood vessel 50. As can be seen in FIG. 5, the measured electrocardiogram is clear and provides clinically useful information.

The electrocardiogram shown in FIG. 6 was measured between (a) a can implanted in the chest of the dog on the right thoracic side, over the pectoralis major muscle, inferior to the clavicle bone and (b) a nerve-facing ring electrode contact surface of an electrode cuff similar to electrode cuff 120 described hereinabove with reference to FIG. 3. The electrode cuff was placed around the cervical vagus nerve at a cervical location in proximity to the right jugular vein approximately 30 cm from the can. This configuration was similar to the embodiment described hereinabove with reference to FIG. 1, in which the cardiac signal is sensed using (a) the outer surface of metal body 34 of the can serving as first sensing electrode contact surface 38, and (b) one of the nerve-facing electrode contact surfaces of electrode device 22. As can be seen in FIG. 6, the measured electrocardiogram is clear and provides clinically useful information.

The electrocardiogram shown in FIG. 7 was measured between two electrode contact surfaces within two respective cuffs placed around the cervical jugular vein such that the two electrode contact surfaces were 2 cm apart from one another. The cuffs were similar to the nerve cuffs described hereinabove with reference to FIG. 3, except that the cuffs were applied to a blood vessel rather than a nerve. This configuration was similar to the embodiment described hereinabove with reference to FIG. 1, in which the cardiac signal is sensed using two blood-vessel facing electrode contact surfaces of two respective blood vessel cuffs. As can be seen in FIG. 7, the measured electrocardiogram is clear and provides clinically useful information.

As used in the present patent application, including in the claims, "longitudinal" means along the length of, and does not mean "around" or "circumferential." For example, "longitudinal positions" along the housing means positions along the length of the housing, rather than positions arranged circumferentially around a longitudinal axis of the housing or the nerve. Such longitudinal positions might be measured in mm from one end of the housing.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/383,157 to Ayal et al., filed May 23, 2002, entitled, "Inverse recruitment for autonomic nerve systems,"

International Patent Application PCT/IL02/00068 to Cohen et al., filed Jan. 23, 2002, entitled, "Treatment of disorders by unidirectional nerve stimulation," and U.S. patent application Ser. No. 10/488,334, in the national stage thereof, U.S. patent application Ser. No. 09/944,913 to Cohen and Gross, filed Aug. 31, 2001, entitled, "Treatment of disorders by unidirectional nerve stimulation," which issued as U.S. Pat. No. 6,684,105, U.S. patent application Ser. No. 09/824,682 to Cohen and Ayal, filed Apr. 4, 2001, entitled "Method and apparatus for selective control of nerve fibers,"

U.S. patent application Ser. No. 10/205,475 to Gross et al., filed Jul. 24, 2002, entitled, "Selective nerve fiber stimulation for treating heart conditions,"

U.S. patent application Ser. No. 10/205,474 to Gross et al., filed Jul. 24, 2002, entitled, "Electrode assembly for nerve control," which issued as U.S. Pat. No. 6,907,295, International Patent Application PCT/IL03/00431 to Ayal et al., filed May 23, 2003, entitled, "Selective nerve fiber stimulation for treating heart conditions,"

International Patent Application PCT/IL03/00430 to Ayal et al., filed May 23, 2003, entitled, "Electrode assembly for nerve control," and U.S. patent application Ser. No. 10/529,149, in the national stage thereof, U.S. patent application Ser. No. 10/719,659 to Ben David et al., filed Nov. 20, 2003, entitled, "Selective nerve fiber stimulation for treating heart conditions,"

U.S. patent application Ser. No. 11/022,011 to Cohen et al., filed Dec. 22, 2004, entitled, "Construction of electrode assembly for nerve control,"

U.S. patent application Ser. No. 11/234,877 to Ben-David et al., filed Sep. 22, 2005, entitled, "Selective nerve fiber stimulation,"

U.S. patent application Ser. No. 11/280,884 to Ayal et al., filed Nov. 15, 2005, entitled, "Techniques for nerve stimulation," which published as US Patent Application Publication 2006/0106441, and a U.S. patent application filed Jul. 9, 2008, entitled, "Electrode cuffs."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   an electrode cuff, which comprises:
   a housing, which is configured to be placed around a nerve of a subject at a first location neither within nor in contact with a heart of the subject; and
   one or more cuff first electrode contact surfaces, which are fixed to the housing;
   at least one second electrode contact surface, which is not directly mechanically coupled to the electrode cuff, and which is configured to be positioned in a body of the subject at a second location neither within nor in contact with the heart; and
   a control unit, which comprises:
   a sensing unit, which is configured to sense, using (a) at least one of the cuff first electrode contact surfaces and (b) the at least one second electrode contact surface, an electrical signal between (a) the at least one of the cuff first electrode contact surfaces and (b) the at least one second electrode contact surface; and
   an analysis unit, which is configured to analyze the signal to identify a parameter of a cardiac cycle of the subject.

2. The apparatus according to claim 1, wherein the at least one second electrode contact surface is directly mechanically coupled to the control unit.

3. The apparatus according to claim 1, wherein the control unit comprises a metal can having an outer conductive surface, at least a portion of which serves as the at least one second electrode contact surface.

4. The apparatus according to claim 1, wherein the housing, when placed around the nerve, is shaped so as to define an outer surface of the electrode cuff and an inner surface that faces the nerve, and wherein the one or more cuff first electrode contact surfaces are fixed to the inner surface of the housing.

5. The apparatus according to claim 1, wherein the housing, when placed around the nerve, is shaped so as to define an outer surface of the electrode cuff and an inner surface that faces the nerve, and wherein the one or more cuff first electrode contact surfaces are fixed to the outer surface of the housing.

6. The apparatus according to claim 1, wherein the nerve is the vagus nerve, and wherein the housing is configured to be placed around the vagus nerve.

7. The apparatus according to claim 1, wherein the control unit comprises a driving unit, which is configured to drive at least some of the cuff first electrode contact surfaces to apply electrical stimulation to the nerve, and configure the stimulation responsively to the parameter of the cardiac cycle.

8. The apparatus according to claim 7,
   wherein the cuff first electrode contact surfaces comprise one or more stimulating cuff first electrode contact surfaces and one or more sensing stimulating cuff first electrode contact surfaces,
   wherein the driving unit is configured to drive the stimulating cuff first electrode contact surfaces, and not the sensing stimulating cuff first electrode contact surfaces, to apply the stimulation, and
   wherein the sensing unit is configured to sense the electrical signal using the sensing cuff first electrode contact surfaces, and not using the stimulating cuff first electrode contact surfaces.

9. The apparatus according to claim 7, wherein the parameter of the cardiac cycle is indicative of ventricular contraction, and wherein the driving unit is configured to drive the at least some of the cuff first electrode contact surfaces to apply the stimulation during at least one heart beat after a delay from the ventricular contraction, the delay having a duration of at least 20 ms.

10. The apparatus according to claim 1, further comprising at least one lead coupled to the control unit, wherein the at least one second electrode contact surface is directly mechanically coupled to the lead.

11. The apparatus according to claim 10, wherein the at least one lead couples the electrode cuff to the control unit, and wherein the at least one second electrode contact surface is directly mechanically coupled to the lead at a position between the electrode cuff and the control unit.

12. A method comprising:
    placing a housing of an electrode cuff around a nerve of a subject at a first location neither within nor in contact with a heart of the subject; and
    implanting a control unit configured to sense, between the electrode cuff and a second location within a body of the subject neither within nor in contact with the heart, a signal indicative of a parameter of a cardiac cycle of the subject, using (a) at least one cuff first electrode contact surface fixed to a housing of the electrode cuff and (b) at least one second electrode contact surface at the second location.

13. The method according to claim 12, wherein sensing comprises sensing using an implanted control unit, and wherein the second location is at the control unit.

14. The method according to claim 12, wherein the nerve is a vagus nerve, and wherein placing comprises placing the housing of the electrode cuff around the vagus nerve.

15. The method according to claim 12, wherein placing the housing of the electrode device comprises placing the housing around the nerve, so as to define an outer surface of the electrode cuff and an inner surface that faces the nerve, and wherein sensing comprises sensing using at least one electrode contact surface that is fixed to the inner surface of the housing.

16. The method according to claim 12, wherein placing the housing of the electrode device comprises placing the housing around the nerve, so as to define an outer surface of the electrode cuff and an inner surface that faces the nerve, and wherein sensing comprises sensing using at least one electrode contact surface that is fixed to the outer surface of the housing.

17. The apparatus according to claim 1, wherein the analysis unit is configured to identify one or more components of an electrocardiogram (ECG) of the heart.

18. The method according to claim 12, wherein implanting the control unit comprises implanting the control unit that is configured to sense one or more components of an electrocardiogram (ECG) of the heart.

19. The method according to claim 12, wherein implanting the control unit comprises implanting at least one lead that couples the electrode cuff to the control unit, and wherein the at least one second electrode contact surface is directly mechanically coupled to the lead at a position between the electrode cuff and the control unit.

20. The method according to claim 15,
    wherein placing the housing around the nerve comprises placing the housing around the nerve, so as to define the outer surface of the electrode cuff and the inner surface that faces the nerve, and two end insulating elements at respective longitudinal positions along the housing, which end insulating elements protrude from the inner surface of the housing toward the nerve so as to electrically isolate a portion of the nerve within the electrode cuff from a portion of the nerve outside the electrode cuff, and wherein sensing comprises sensing using the at least one electrode contact surface that is fixed to the inner surface of the housing longitudinally between the two end insulating elements.

21. The apparatus according to claim 4, wherein the housing, when placed around the nerve, is shaped so as to further define two end insulating elements at respective longitudinal positions along the housing, which end insulating elements protrude from the inner surface of the housing toward the nerve so as to electrically isolate a portion of the nerve within the electrode cuff from a portion of the nerve outside the electrode cuff, and wherein the one or more cuff first electrode contact surfaces are fixed to the inner surface of the housing longitudinally between the two end insulating elements.

* * * * *